US009456803B2

(12) United States Patent
Nakamura et al.

(10) Patent No.: US 9,456,803 B2
(45) **Date of Patent: *Oct. 4, 2016**

(54) ULTRASONIC PROBE AND ULTRASONIC INSPECTION APPARATUS

(71) Applicant: SEIKO EPSON CORPORATION, Tokyo (JP)

(72) Inventors: Tomoaki Nakamura, Nagano (JP); Hiroaki Hosomi, Minowa-machi (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/859,901

(22) Filed: Sep. 21, 2015

(65) Prior Publication Data

US 2016/0007963 A1 Jan. 14, 2016

Related U.S. Application Data

(63) Continuation of application No. 13/917,118, filed on Jun. 13, 2013, now Pat. No. 9,168,025.

(30) Foreign Application Priority Data

Jun. 15, 2012 (JP) ................................ 2012-135522

(51) Int. Cl.
*A61B 8/00* (2006.01)
*B06B 1/06* (2006.01)

(52) U.S. Cl.
CPC .......... *A61B 8/4494* (2013.01); *A61B 8/4444* (2013.01); *B06B 1/0629* (2013.01); *B06B 1/0674* (2013.01)

(58) Field of Classification Search
CPC .. A61B 8/444; A61B 8/4494; B06B 1/0629; B06B 1/0674
See application file for complete search history.

(56) References Cited

U.S. PATENT DOCUMENTS

| | | | |
|---|---|---|---|
| 8,169,855 | B2 | 5/2012 | Nakamura |
| 8,344,595 | B2 | 1/2013 | Funasaka et al. |
| 2011/0115337 | A1 | 5/2011 | Nakamura et al. |
| 2011/0227449 | A1 | 9/2011 | Nakamura |
| 2012/0306316 | A1 | 12/2012 | Nakamura et al. |

FOREIGN PATENT DOCUMENTS

| | | | |
|---|---|---|---|
| JP | 2006-075425 | A | 3/2006 |
| JP | 2006-319945 | A | 11/2006 |
| JP | 2009-055644 | A | 3/2009 |
| JP | 2010-165341 | A | 7/2010 |
| JP | 2010-183437 | A | 8/2010 |
| JP | 2010-210283 | A | 9/2010 |
| JP | 2011-124973 | A | 6/2011 |
| JP | 2011-217351 | A | 10/2011 |
| JP | 2012-253405 | A | 12/2012 |

*Primary Examiner* — Michael Rozanski
(74) *Attorney, Agent, or Firm* — Global IP Counselors, LLP

(57) ABSTRACT

An ultrasonic probe includes a substrate, a diaphragm, a thin-film piezoelectric element, a communication passage, and an air hole. The substrate has first and second cavities thereon. The diaphragm is configured at the first cavity. The thin-film piezoelectric element is configured to the diaphragms. The communicating passage is configured in the substrate and extending from the first cavity to the second cavity. The air hole extends between the communicating passage to an outside of the substrate.

7 Claims, 5 Drawing Sheets

ULTRASONIC PROBE AND ULTRASONIC INSPECTION APPARATUS

CROSS-REFERENCE TO RELATED APPLICATIONS

This application is a continuation application of U.S. patent application Ser. No. 13/917,118, filed on Jun. 13, 2013, now U.S. Pat. No. 9,168,025. This application claims priority to Japanese Patent Application No. 2012-135522 filed on Jun. 15, 2012. The entire disclosures of U.S. patent application Ser. No. 13/917,118 and Japanese Patent Application No. 2012-135522 is hereby incorporated herein by reference.

BACKGROUND

1. Technical Field

The present invention relates to an ultrasonic probe and to an ultrasonic inspection apparatus.

2. Related Art

In an ultrasonic probe using a thin-film piezoelectric element, a well-known structure is as illustrated in, for example, FIG. 3 of Patent Document 1, where a cavity space (17 in the drawing) is a sealed enclosed space. In the case of such a structure, when the cavity space is narrow, in some cases it becomes difficult to freely move a diaphragm, and there is a decline in the operating properties.

Japanese Laid-open Patent Publication No. 2006-75425 (Patent Document 1) is an example of the related art.

SUMMARY

An advantage of the invention is to provide an ultrasonic probe and an ultrasonic inspection apparatus making it possible to prevent a decline in the operating properties of a diaphragm and to possess favorable transmission and reception properties.

According to one aspect of the invention, an ultrasonic probe includes a substrate, a diaphragm, a thin-film piezoelectric element, a communication passage, and an air hole. The substrate has first and second cavities thereon. The diaphragm is configured at the first cavity. The thin-film piezoelectric element is configured to the diaphragms. The communicating passage is configured in the substrate and extending from the first cavity to the second cavity. The air hole extends between the communicating passage to an outside of the substrate.

BRIEF DESCRIPTION OF THE DRAWINGS

Referring now to the attached drawings which form a part of this original disclosure.

DETAILED DESCRIPTION OF EXEMPLARY EMBODIMENTS

The following describes in greater detail the ultrasonic transducer, the ultrasonic probe, and the ultrasonic inspection apparatus of the invention, on the basis of a preferred embodiment illustrated in the accompanying drawings.

Embodiment of the Ultrasonic Transducer and the Ultrasonic Probe

Figure 1:
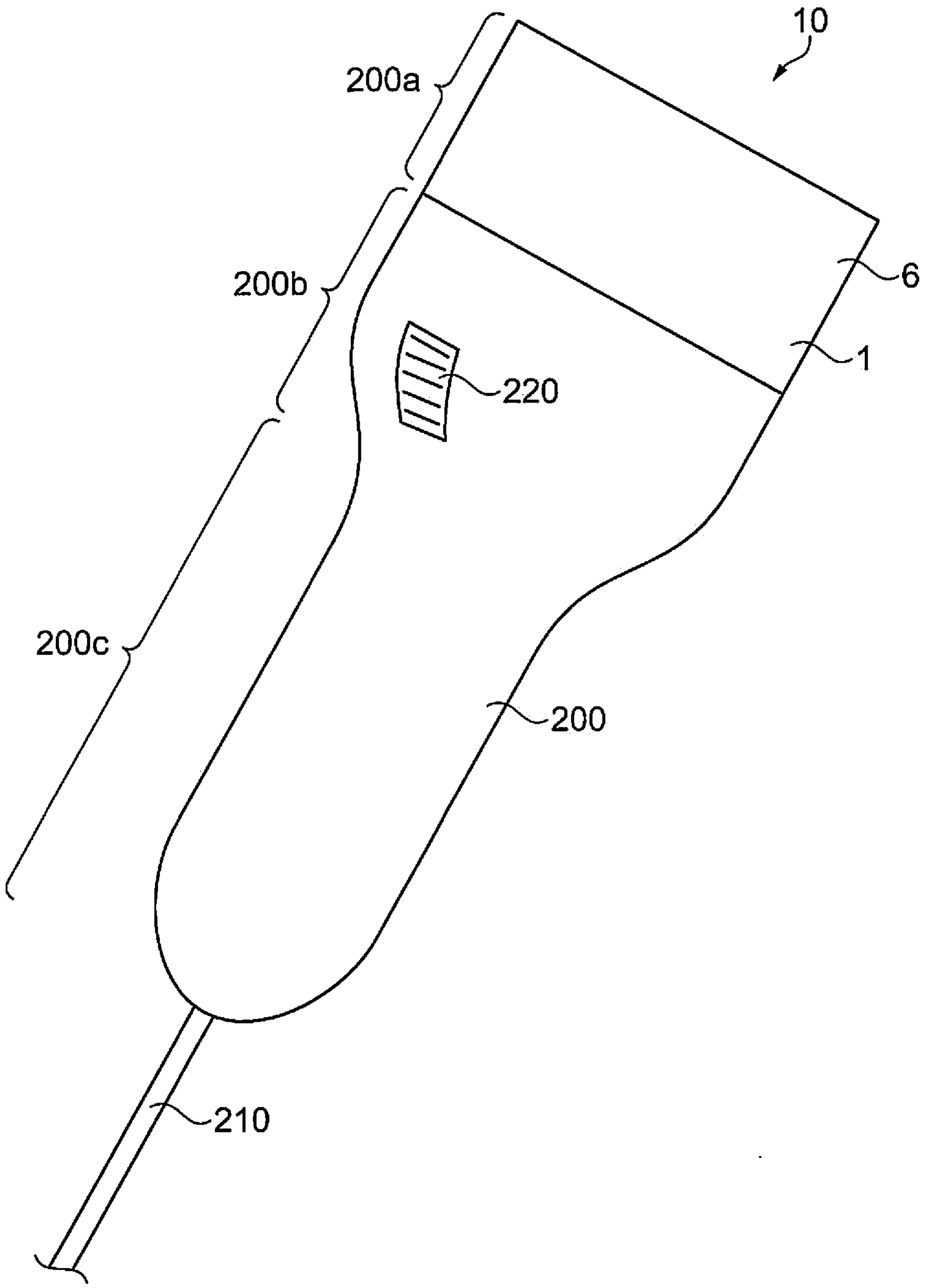
FIG. 1 is a perspective view illustrating an embodiment of an ultrasonic probe of the invention.
Figure 2:
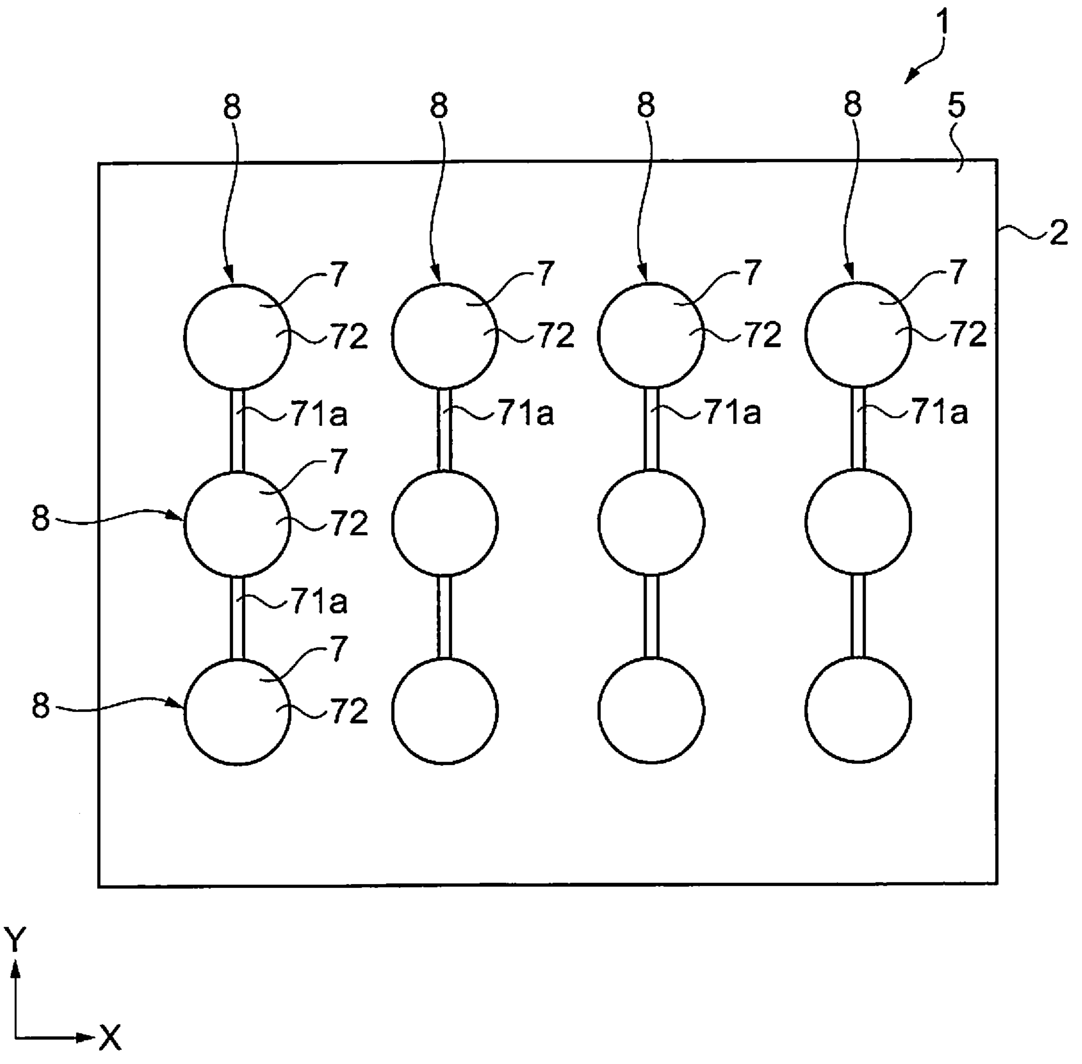
FIG. 2 is a plan view illustrating an ultrasonic transducer of the ultrasonic probe illustrated in FIG. 1.
Figure 3:
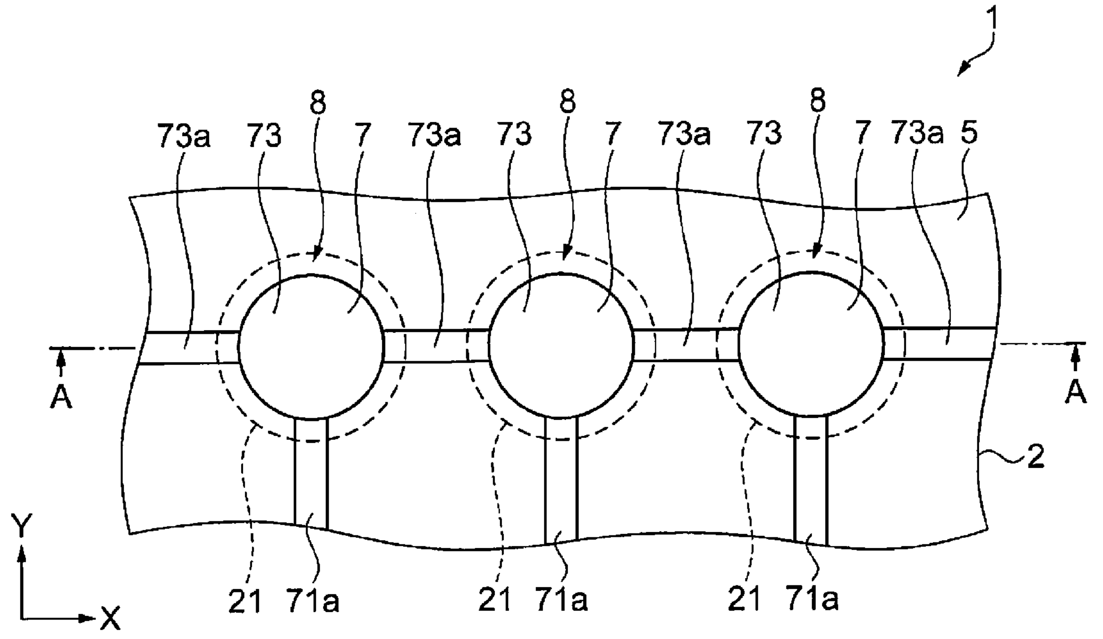
FIG. 3 is a plan view illustrating an enlarged part of the ultrasonic transducer illustrated in FIG. 2.
Figure 4:
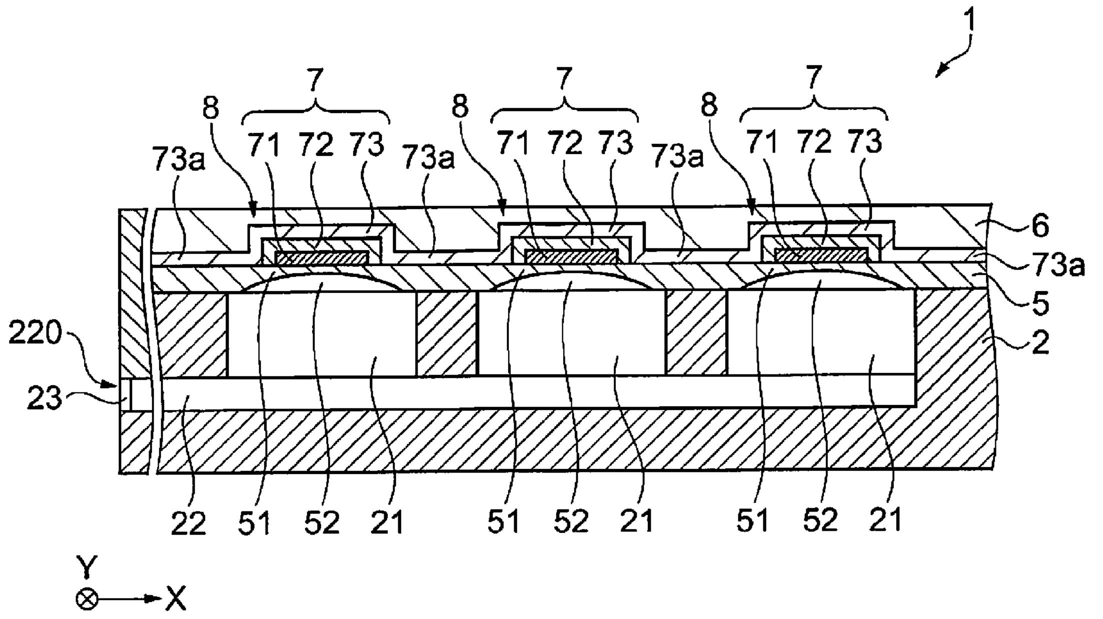
FIG. 4 is a cross-sectional view taken along the A-A line in FIG. 3.
Figure 5:
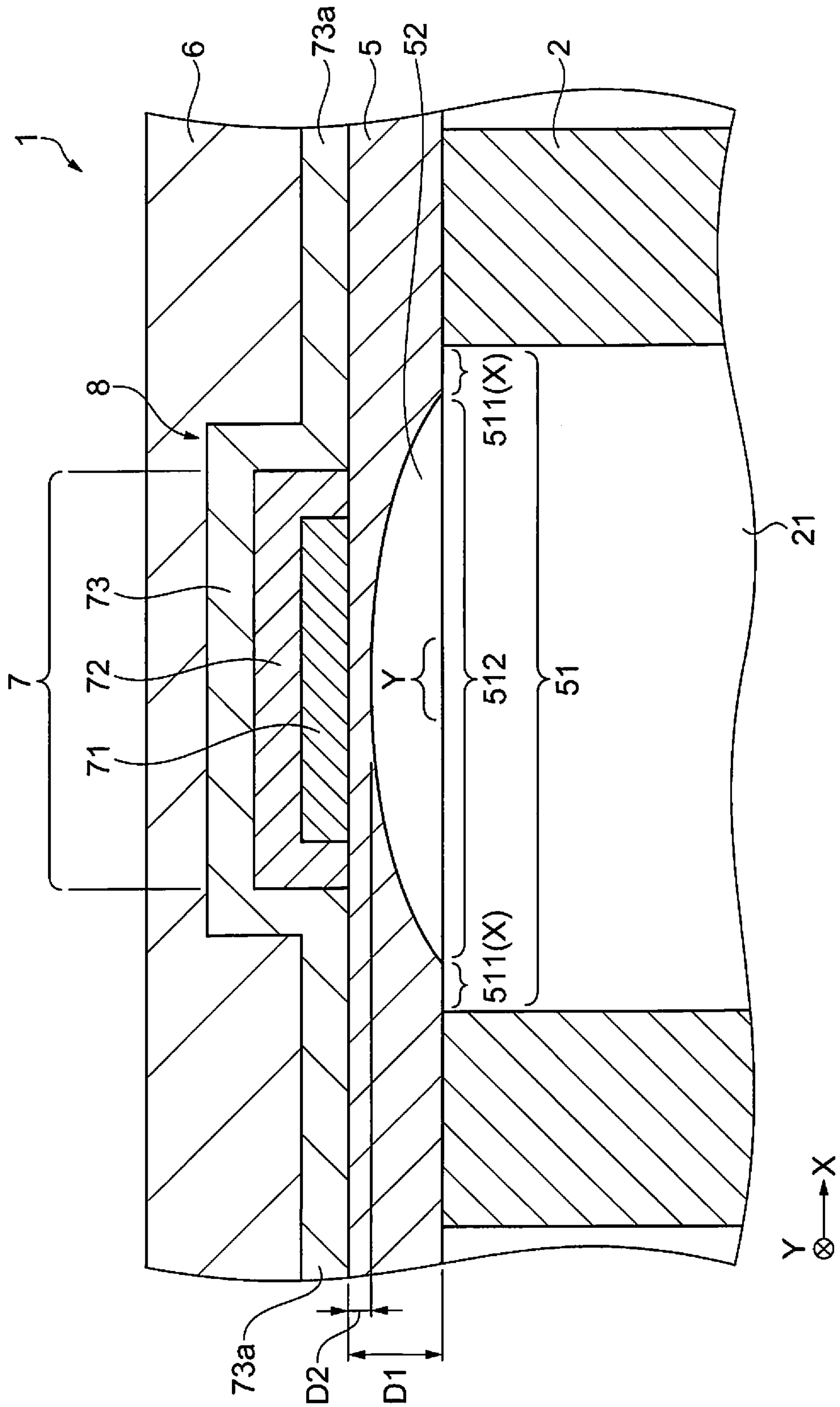
FIG. 5 is a cross-sectional view illustrating an enlarged part of the ultrasonic transducer illustrated in FIG. 4.

FIG. 1 is a perspective view illustrating an embodiment of an ultrasonic probe of the invention; FIG. 2 is a plan view illustrating an ultrasonic transducer of the ultrasonic probe illustrated in FIG. 1; FIG. 3 is a plan view illustrating an enlarged part of the ultrasonic transducer illustrated in FIG. 2; FIG. 4 is a cross-sectional view taken along the A-A line in FIG. 3; and FIG. 5 is a cross-sectional view illustrating an enlarged part of the ultrasonic transducer illustrated in FIG. 4. The following describes the upper side in FIGS. 3 to 5 as being "up" or "above", the lower side as being "down" or "below", the right side as being "right", and the left side as being "left".

FIG. 2 is a schematic illustration of the ultrasonic transducer, partially omitting a depiction of an acoustic matching unit, an upper electrode, a lower electrode, an upper electrode conductor, a lower electrode conductor, and the like. FIG. 3 omits a depiction of the acoustic matching unit. Also, as illustrated in each of the drawings, an X-axis and Y-axis that are orthogonal to each other are assumed. The X-axis direction corresponds to an azimuth direction and the Y-axis direction corresponds to a slice direction.

As illustrated in FIG. 1, an ultrasonic probe 10 has a housing 200 and an ultrasonic transducer 1 housed in the housing 200. The ultrasonic transducer 1 is installed at a distal end of the housing 200. The ultrasonic probe 10 can be used as an ultrasonic probe for a variety of ultrasonic inspection apparatuses, such as, for example, an ultrasonic inspection apparatus 100 (described below).

Also, in the present embodiment, the surface of the ultrasonic transducer 1, i.e., the surface of an acoustic matching unit 6 (described below) is exposed to the exterior. The acoustic matching unit 6 functions as a protective layer of the ultrasonic probe 10 and the ultrasonic transducer 1. Though not particularly limited, a material having substantially the same acoustic impedance as that of the human body, e.g., silicone rubber or the like is used as the constituent material of the acoustic matching unit 6. The configuration can also be such that the surface of the acoustic matching unit 6 is exposed to the exterior.

During inspection, the ultrasonic probe 10 is used by abutting the surface of the acoustic matching unit 6 against a biological body intended to be inspected. In such a case, when ultrasonic waves are sent from the ultrasonic transducer 1 toward the acoustic matching unit 6, the ultrasonic waves pass through the acoustic matching unit 6 and propagate to the interior of the biological body; ultrasonic waves reflected at a predetermined site within the biological body pass through the acoustic matching unit 6 and are inputted to the ultrasonic transducer 1.

The ultrasonic probe 10 is also electrically connected to an apparatus main body 300 (see FIG. 6) of the ultrasonic inspection apparatus 100 (described below) via a cable 210. Air holes 220 are provided to a part of the housing 200 of the ultrasonic probe 10. The ultrasonic probe 10 has a sensing unit 200*a* to be brought into contact with a inspection test object and a grip section 200*c* that is gripped by an operator; the sensing unit 200*a* and the grip section 200*c* are linked to each other at an intermediate section 200*b*. The air holes 220 are arranged at the intermediate section 200*b*, with an external design that prevents the operator from unintentionally blocking off the air holes 200.

As illustrated in FIGS. 2 to 5, the ultrasonic transducer 1 used in the ultrasonic probe of the invention is provided with: a substrate 2; a plurality (12 in number in the configuration depicted) of ultrasonic elements (ultrasonic vibrators) 8 for sending and receiving ultrasonic waves, the ultrasonic elements being provided on the substrate 2; and the acoustic matching unit 6 for covering the ultrasonic elements 8, the acoustic matching unit being provided on a side of the substrate 2 closer to the ultrasonic elements 8.

Though not particularly limited, the shape of the substrate 2 forms a quadrangle as seen in plan view in the configuration depicted. Other possible examples of the shape of the substrate 2 as seen in plan view include other polygons, such as a pentagon or a hexagon, as well as a circle, and ellipse, and the like. Also, a semiconductor formation material such as, for example, silicon (Si) is used as the constituent material of the substrate 2, though not particularly limited thereto. This makes processing by etching or the like readily possible.

The ultrasonic elements 8 are constituted of a diaphragm 51 and a thin-film piezoelectric element 7, and the ultrasonic elements 8 are arranged in rows and columns on the substrate 2. That is, a plurality of the ultrasonic elements 8 (four in number in the configuration depicted) are arranged side by side along the X-axis direction, and a plurality (three in number in the configuration depicted) are arranged side by side along the Y-axis direction.

Though not particularly limited, the shape of the thin-film piezoelectric elements 7 forms a circle as seen in plan view in the configuration depicted. Other possible examples of the shape of the thin-film piezoelectric elements 7 as seen in plan view include other polygons, such as a quadrangle (a square or rectangle), a pentagon or a hexagon, as well as an ellipse and the like. The thin-film piezoelectric elements 7 and the wiring therefor shall be described below. Formed at sites of the substrate 2 that correspond to each of the ultrasonic elements 8 are cavities 21 at each of which there is an opening for forming the diaphragm 51 of the ultrasonic element 8.

Though not particularly limited, the shape of the cavities 21 forms a circle as seen in plan view in the configuration depicted. Other possible examples of the shape of the cavities 21 as seen in plan view include polygons, such as a quadrangle (a square or rectangle), a pentagon or a hexagon, as well as an ellipse and the like. In the cavities 21, a communicating passage 22 is provided to the opposite side of a support film 5, forming a structure in all of the cavities 21 through which air communicates. The communicating passage 22 is linked to the air holes 220 provided to an exterior covering portion of the ultrasonic probe 10. A semipermeable membrane 23 that is permeable to gases but not permeable to liquids or solids is provided to the air holes 220. One example used as a material for the semipermeable membrane is a porous ultra-high-molecular weight polyethylene film achieved by preparing and then cutting a sintered porous compact of ultra-high-molecular-weight polyethylene powder.

Generally, when the number of the diaphragms is increased and a higher density is implemented, each of the diaphragms 51 will be smaller in size, and each of the cavities 21 will be smaller in volume. In a case where a higher density of the cavities 21 is implemented within an enclosed space, it becomes difficult for the diaphragms 51 to move. However, in the structure described above, the cavities 21 are not in an enclosed space but rather communicate with the outside air, and thus even when the cavities 21 are smaller in volume, it does not become difficult for the diaphragms 51 to move, nor is there a decline in the operating properties. That is, in the present configuration, it is possible to obtain favorable transmission and reception properties imparted by the diaphragms 51.

The embodiment describes an example where the communicating passage 22 communicates (or extends) through all of the cavities 21, but the communicating passage need not necessarily communicate (or extends) through all of the cavities. For example, in a case such as where the volume of several cavities could be set to a sufficiently large volume, it would not be difficult for the diaphragms provided to the cavities to move, and thus in some cases there need not be communication therewith. In the invention, the structure need only be such that only cavities of a sufficiently smaller volume for there to be a decline in the operating properties of the diaphragms are communicated to allow air to pass through to the outside environment of the ultrasonic probe 10, i.e., a structure that communicates with the atmosphere.

The support film 5 is formed on the substrate 2, and each of the cavities 21 is closed off by the support film 5. The diaphragms 51 are constituted of opening corresponding sites, which are sites (regions) of the support film 5 at which the cavities 21 are closed off, i.e., sites of the support film 5 that are matched to (alternatively, sites that overlap with) the cavities 21 as seen in plan view. The thin-film piezoelectric elements 7 are provided on the diaphragms 51.

Though the constituent material of the support film 5 is not particularly limited, the support film 5 is constituted of, for example, a laminate (two-layer structure) of an $SiO_2$ film and a $ZrO_2$ layer, an $SiO_2$ film, or the like. Herein, in a case where the substrate 2 is an Si substrate, the $SiO_2$ layer could be formed by a thermal oxidation treatment of the surface of the substrate 2. The $ZrO_2$ layer could be formed on the $SiO_2$ layer by, for example, a technique such as sputtering. Herein, in a case where, for example, lead zirconate titanate (PZT) is used as a piezoelectric film 72 of the thin-film piezoelectric elements 7 (described below), then the $ZrO_2$ layer would be a layer for preventing the Pb constituting the PZT from being diffused into the $SiO_2$ layer. The $ZrO_2$ layer also has such effects as enhancing a flexing efficiency with respect to strain of the piezoelectric film 72.

The thin-film piezoelectric elements 7 have a lower electrode 71 formed on the diaphragms 51 (the support film 5), the piezoelectric film 72 formed on the lower electrode 71, and an upper electrode 73 formed on the piezoelectric film 72.

Connected to the lower electrodes 71 are lower electrode conducting wires 71*a* extending along the Y-axis direction on the support film 5, as illustrated in, for example, FIG. 3. The lower electrode conducting wires 71*a* are shared conducting wires of ultrasonic elements 8 that are arranged side by side in the Y-axis direction. That is, a lower electrode conducting wire 71*a*, as illustrated in FIG. 3, is connected to the lower electrodes 71 of ultrasonic elements 8 that are adjacent to each other in the Y-axis direction. This makes it possible for groups of ultrasonic elements 8 that are arranged side by side in the Y-axis direction to be driven independently.

Connected to the upper electrodes 73 are upper electrode conducting wires 73*a* extending along the X-axis direction on the support film 5, as illustrated in, for example, FIG. 3. The upper electrode conducting wires 73*a* are shared conducting wires of ultrasonic elements 8 that are arranged side by side in the X-axis direction. That is, an upper electrode conducting wire 73*a*, as illustrated in FIG. 3, is connected to the upper electrodes 73 of ultrasonic elements 8 that are adjacent to each other in the X-axis direction, and is connected at its end to, for example, ground GND. The upper electrodes 73 of the ultrasonic elements 8 are thereby grounded. The lower electrode conducting wires 71*a* may, however, be connected to the ground GND, inverse to the preceding description.

The constituent materials of the lower electrodes 71, the upper electrodes 73, the lower electrode conducting wires 71*a*, and the upper electrode conducting wires 73*a* are not particularly limited, provided that the materials be electroconductive; for example, a variety of metallic materials or the like could be used. The lower electrodes 71, the upper electrodes 73, the lower electrode conducting wires 71*a*, and the upper electrode conducting wires 73*a* can be single layers or can be laminates obtained by laminating together a plurality of layers. As a specific example, it would be possible, for example, to use a Ti/Ir/Pt/Ti laminate film as the lower electrodes 71 and as the lower electrode conducting wires 71*a*, and to use an Ir film as the upper electrodes 73 and the upper electrode conducting wires 73*a*.

The piezoelectric film 72 is formed, for example, by depositing a film of PZT. Although in the present embodiment PZT is used as the piezoelectric film 72, any material can be used, provided that the material can be contracted (expanded or contracted) in the in-plane direction by applying a voltage; other than PZT, for example, lead titanate ($PbTiO_3$), lead zirconate ($PbZrO_3$), lead lanthanum titanate ($(Pb, La)TiO_3$), or the like can be used.

With the ultrasonic elements 8 of such description, for example, applying a voltage between the lower electrodes 71 and the upper electrodes 73 via the cable 210 using the apparatus main body 300 (see FIG. 6) causes the piezoelectric film 72 to expand or contract in the in-plane direction. At this time, one surface of the piezoelectric film 72 is bonded to the support film 5 via the lower electrodes 71, and the upper electrodes 73 are formed on the other side thereof. Herein, because no other layer is formed on the upper electrodes 73, the side of the piezoelectric film 72 closer to the support film 5 is less readily expanded or contracted, while the side closer to the upper electrodes 73 is more readily expanded or contracted. For this reason, when a voltage is applied to the piezoelectric film 72, a deflection that becomes convex toward the cavities 21 takes place, and the diaphragms 51 are deflected. As such, applying an alternating-current voltage to the piezoelectric film 72 causes the diaphragms 51 to vibrate with respect to a film thickness direction, and the vibration of the diaphragms 51 causes an ultrasonic wave to be transmitted (emitted).

When an ultrasonic wave is transmitted, an alternating-current voltage of a frequency that either is equal to a resonant frequency of the ultrasonic elements 8 or is close to the resonant frequency is applied to the piezoelectric film 72, resulting in resonant drive of the ultrasonic elements 8. This considerably deflects the diaphragms 51 and makes it possible for high-output ultrasonic waves to be transmitted. In a case where ultrasonic waves are received at the ultrasonic elements 8, when the ultrasonic waves are inputted to the diaphragms 51, the diaphragms 51 vibrate in the film thickness direction. With the ultrasonic elements 8, the vibration of the diaphragms 51 causes a difference in electrical potential to occur between the surface of the piezoelectric film 72 closer to the lower electrodes 71 and the surface closer to the upper electrodes 73, and a reception signal (detection signal) corresponding to the amount of displacement of the piezoelectric film 72 is outputted from the upper electrodes 73 and the lower electrodes 71. The signal is transmitted to the apparatus main body 300 (see FIG. 6) via the cable 210, and predetermined signal process or the like is carried out on the basis of the signal at the apparatus main body 300. An ultrasonic image (electronic image) is thereby formed and displayed in the apparatus main body 300.

Also, with the ultrasonic probe 10 of such description, creating a shift by delaying the timing of emitting ultrasonic waves from ultrasonic elements 8 that are provided side by side along the X-axis direction makes it possible to transmit planar waves in a desired direction.

Now, as illustrated in FIG. 5, in the transducer 1, the thickness of the opening corresponding sites of the support film 5 that are matched to the cavities 21 as seen in plan view, i.e., the thickness of center parts of the diaphragms 51 is set to be thinner than the thickness of outer edge parts of the diaphragms 51. In such a case, an annular region X having a predetermined width from an outer peripheral end of the opening corresponding sites of the support film 5 toward the inside of the opening corresponding sites, i.e., towards the center of gravity as seen in plan view serves as the outer edge parts of the opening corresponding sites, while a region Y of a predetermined surface area that excludes the region X (the outer edge parts) and includes a center-of-gravity position of the opening corresponding parts serves as the center part of the opening corresponding sites.

In the present embodiment, the diaphragms 51 have a constant thickness part 511, at which the thickness is constant, at the outer edge parts thereof. The constant thickness parts 511 are provided spanning one lap around the diaphragms 51. That is, the constant thickness parts 511 form an annular shape as seen in plan view. The diaphragms 51 also have a gradually increasing thickness part 512, at which the thickness gradually increases going from the center of gravity of the diaphragms 51 (the center parts) toward the outer edge parts, the gradually increasing thickness parts being continuous with the constant thickness parts 511. That is, a recess 52 having a curved surface (a curved, concave surface) that has been curved in a bowl shape is formed on the lower surface side of the diaphragms 51.

This heightens the strength of the outer edge parts, i.e., the constant thickness parts 511 of the diaphragms 51 and causes the gradually increasing thickness parts 512, especially the center part sides of the gradually increasing thickness parts 512, of the diaphragms 51 to be more readily deflected, thereby making it possible to also prevent damage to the diaphragms 51, such as chipping or cracking, while also possessing favorable transmission and reception properties.

That is, in the transmission and reception of ultrasonic waves, though the resonant drive of the ultrasonic elements 8 during transmission can considerably deflect the diaphragms 51, damage in the vicinity of the outer edge parts of the diaphragms 51, such as chipping or cracking, can still be prevented. Because the center parts of the diaphragm 51 are locally more susceptible to deflection, it is possible to increase the amount of deflection in the thin-film piezoelectric elements 7 during transmission and reception of ultrasonic waves, especially during reception where the diaphragms 51 are deflected by a lesser amount, and this creates a considerable stress in the thin-film piezoelectric elements 7 and makes it possible to enhance the level of reception signal outputted from the thin-film piezoelectric elements 7. That is, the sensitivity during reception of ultrasonic waves can be enhanced.

The thin-film piezoelectric elements 7 are arranged closer to the center part side than the constant thickness parts 511 on the diaphragms 51. This makes it possible to more reliably enhance the sensitivity during reception of ultrasonic waves.

Herein, the dimensions of the diaphragms 51 (the support film 5) are not particularly limited, and are determined as appropriate in accordance with a variety of conditions; however, preferably, a ratio D2/D1 is 0.1 to 0.9, where D1 is the thickness of the constant thickness parts 511 (the outer edges) of the diaphragms 51, and D2 is the thickness of the center-of-gravity positions (centers) of the diaphragms 51 as seen in plan view. This makes it possible to more reliably prevent damage in the vicinity of the outer edge parts of the diaphragms 51, such as chipping or cracking, and also makes it possible to more reliably enhance the sensitivity during reception of ultrasonic waves.

Preferably, the thickness D1 of the constant thickness parts 511 (the outer edges) of the diaphragms 51 is 0.4 to 1.5 μm. This makes it possible to more reliably prevent damage in the vicinity of the outer edge parts of the diaphragms 51, such as chipping or cracking. Preferably, the thickness D2 of the center-of-gravity positions of the diaphragms 51 is 0.15 to 1.35 μm. This makes it possible to more reliably enhance the sensitivity during reception of ultrasonic waves.

Also, preferably, a ratio S1/S2 is 0.02 to 0.25, where S1 is the surface area of the constant thickness parts 511 of the diaphragms 51 and S2 is the surface area of the gradually increasing thickness parts 512. This makes it possible to more reliably prevent damage in the vicinity of the outer edge parts of the diaphragms 51, such as chipping or cracking, and also makes it possible to more reliably enhance the sensitivity during reception of ultrasonic waves. Though the diaphragms 51 have the constant thickness parts 511 in the present embodiment, the constant thickness parts 511 can also be omitted.

Embodiment of the Ultrasonic Inspection Apparatus

Figure 6:
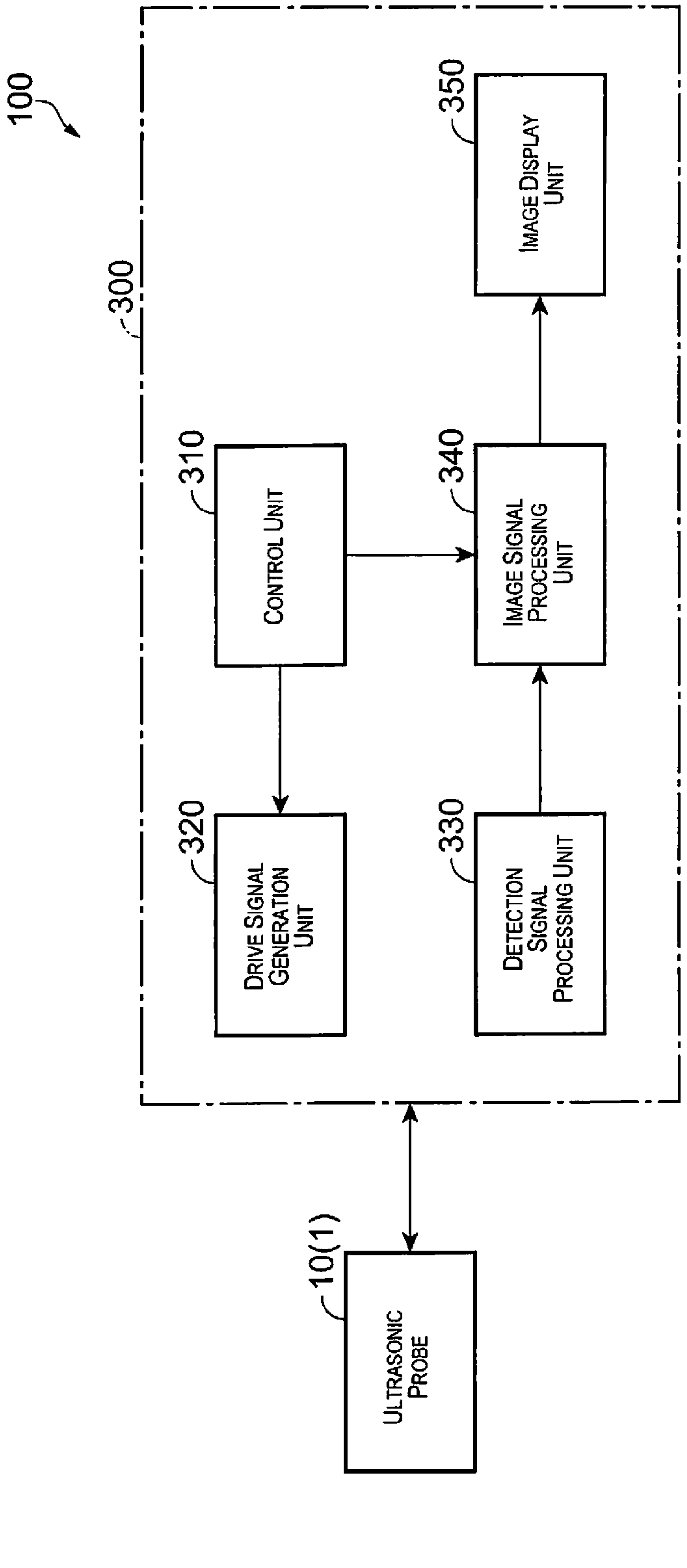
FIG. 6 is a block diagram illustrating an embodiment of an ultrasonic inspection apparatus of the invention.

FIG. 6 is a block diagram illustrating an embodiment of an ultrasonic inspection apparatus of the invention. As illustrated in FIG. 6, the ultrasonic inspection apparatus 100 is provided with the previously described ultrasonic probe 10 and the apparatus main body 300 electrically connected to the ultrasonic probe 10 via the cable 210.

The apparatus main body 300 is provided with a control unit (controlling means) 310, a drive signal generation unit 320, a detection signal processing unit 330, an image signal processing unit 340, and an image display unit (displaying means) 350. The detection signal processing unit 330 and the image signal processing unit 340 constitute a signal processing unit.

The control unit 310 is constituted of, for example, a microcomputer or the like, and controls the entirety of the apparatus main body 300, including the drive signal generation unit 320 and the image signal processing unit 340. The image display unit 350 is constituted of, for example, a display device such as a cathode ray tube (CRT) or liquid crystal display (LCD).

Next, a description will be given of the operation of the ultrasonic inspection apparatus 100. During inspection, the surface of the acoustic matching unit 6 of the ultrasonic probe 10 is abutted against a biological body that is to be inspected, and the ultrasonic inspection apparatus 100 is activated.

First, when the control unit 310 outputs a transmission instruction to the drive signal generation unit 320, the drive signal generation unit 320 sends to the ultrasonic elements 8 drive signals for driving the ultrasonic elements each at a predetermined timing. Each of the ultrasonic elements 8 is thereby driven at a predetermined timing. This results in ultrasonic waves being emitted from the ultrasonic transducer 1 of the ultrasonic probe 10.

The ultrasonic waves thus emitted propagate within the interior of the biological body, and ultrasonic waves that are reflected at a predetermined site within the biological body are inputted to the ultrasonic transducer 1 of the ultrasonic probe 10. A detection signal corresponding to the inputted ultrasonic waves is then outputted from the ultrasonic transducer 1. The detection signal is transmitted to the detection signal processing unit 320 of the apparatus main body 300 via the cable 210, is subjected to predetermined signal processing in the detection signal processing unit 320, and is converted to a digital signal by an A/D converter (not shown) included in the detection signal processing unit 320.

The digital signal outputted from the detection signal processing unit 320 is inputted to the image signal processing unit 340 and, in synchronism with a frame timing signal, is stored sequentially as surface data in a primary storage unit (not shown) included in the image signal processing unit 340. The image signal processing unit reconstructs two-dimensional or three-dimensional image data on the basis of respective surface data, and also subjects the image data to image processing such as, for example, interpolation, response enhancement processing, or gradation processing. Having undergone the image processing, the image data is stored in a secondary storage unit (not shown) included in the image signal processing unit 340.

The image data having undergone the image processing is then read out from the secondary storage unit of the image signal processing unit 340 and inputted to the image display unit 350. The image display unit 350 displays an image on the basis of the image data. A health care professional, such as a physician, carries out diagnoses or the like by viewing the image displayed on the image display unit 350.

The foregoing describes the ultrasonic probe and the ultrasonic inspection apparatus of the invention on the basis of the embodiment depicted, but the invention is in no way limited thereto, but rather the configurations of each of the parts can be replaced with any desired configuration that has a similar functionality. Any other desired component(s) can also be added to the invention.

In the embodiment described above, there were a plurality of the ultrasonic elements, i.e., pluralities of the piezoelectric elements and the opening corresponding sites of the support film; however, there is no limitation thereto in the invention, and the ultrasonic element can also be singular in number.

According to the embodiment, an ultrasonic probe includes an ultrasonic device, and a housing. The housing for supporting the ultrasonic device. The ultrasonic device includes a substrate having first and second cavities, a diaphragm being configured at the first cavity, a thin-film piezoelectric element being configured to the diaphragm, and a communicating passage being configured in the substrate and extending from the first cavity to the second cavity. The housing includes an air hole extending between an interior and an exterior of the housing.

GENERAL INTERPRETATION OF TERMS

In understanding the scope of the present invention, the term “comprising” and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, “including”, “having” and their derivatives. Also, the terms “part,” “section,” “portion,” “member” or “element” when used in the singular can have the dual meaning of a single part or a plurality of parts. Finally, terms of degree such as “substantially”, “about” and “approximately” as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic probe comprising:

a substrate having first and second cavities that are not formed of electrodes;

a first ultrasonic element disposed over the substrate and overlapping with the first cavity when viewed along a thickness direction of the substrate, the first ultrasonic element including a first diaphragm facing the first cavity; and a second ultrasonic element disposed over the substrate and overlapping with the second cavity when viewed along the thickness direction of the substrate, the second ultrasonic element including a second diaphragm facing the second cavity;

the substrate further having a communicating passage and an air hole, the first cavity being communicated with the second cavity through the communicating passage, the communicating passage being communicated with an outside of the substrate through the air hole, the first ultrasonic element being configured to transmit or receive ultrasonic waves, and the second ultrasonic element being configured to transmit or receive ultrasonic waves.

2. The ultrasonic probe as set forth in claim 1, further comprising a housing which accommodates the substrate, the first ultrasonic element and the second ultrasonic element, wherein the air hole is arranged in an outer peripheral surface of the housing, the substrate includes a semipermeable film at the air hole, and the semipermeable film is permeable to gas but is not permeable to liquid and solid.

3. The ultrasonic probe as set forth in claim 1, wherein the substrate includes a third cavity, and the communicating passage extends to all the first, second, and third cavities.

4. The ultrasonic probe as set forth in claim 1, wherein a surface of each of the first diaphragm and the second diaphragm on a side facing the first cavity and the second cavity, respectively, is a concave surface that is curved.

5. The ultrasonic probe as set forth in claim 1, wherein the first ultrasonic element includes a first piezoelectric element disposed over the first diaphragm, and the second ultrasonic element includes a second piezoelectric element disposed over the second diaphragm.

6. An ultrasonic inspection apparatus comprising:

the ultrasonic probe as in claim 1; and an apparatus main body having a signal processor being configured to carry out signal processing on the basis of a signal that is transmitted from the ultrasonic probe.

7. An ultrasonic probe comprising:

an ultrasonic device; and a housing supporting the ultrasonic device, the ultrasonic device including a substrate having first and second cavities that are not formed of electrodes, a first ultrasonic element disposed over the substrate and overlapping with the first cavity when viewed along a thickness direction of the substrate, the first ultrasonic element including a first diaphragm facing the first cavity, and a second ultrasonic element disposed over the substrate and overlapping with the second cavity when viewed along the thickness direction of the substrate the second ultrasonic element including a second diaphragm facing the second cavity, the substrate further having a communicating passage, the first cavity being communicated with the second cavity through the communicating passage, the housing having an air hole, an interior of the housing being communicated with an exterior of the housing through the air hole.

* * * * *